United States Patent [19]

Dessapt

[11] Patent Number: 4,835,746

[45] Date of Patent: May 30, 1989

[54] DEVICE FOR PRODUCING SOUNDWAVES IN WATER

[75] Inventor: Jean-Paul Dessapt, Beynes, France

[73] Assignee: Institut Francais du Petrole, Rueil-Malmaison, France

[21] Appl. No.: 55,924

[22] Filed: Jun. 1, 1987

Related U.S. Application Data

[63] Continuation-in-part of Ser. No. 694,056, Jan. 23, 1985, abandoned.

[30] Foreign Application Priority Data

Jan. 24, 1984 [FR] France .................................. 84 10169

[51] Int. Cl.⁴ .............................................. G01V 1/14
[52] U.S. Cl. ..................... 367/146; 367/144; 181/120
[58] Field of Search ................ 367/144, 146; 181/119, 181/120, 115

[56] References Cited

U.S. PATENT DOCUMENTS 4,594,697  6/1986  Pascouet .
4,733,382  3/1988  Pascouet .............................. 367/146

Primary Examiner—Deborah L. Kyle
Assistant Examiner—John Woodrow Eldred
Attorney, Agent, or Firm—Antonelli, Terry & Wands

[57] ABSTRACT

An apparatus for producing acoustic waves in water through sudden ejection of liquid mass from a tubular main housing. A first shuttle and second shuttle are slidably mounted inside the main housing. The first shuttle forms with the main housing a slug chamber for confining therein a liquid slug. A pneumatic source together with a pneumatically-operated valve cyclically cause the shuttles to move relative to or in locked condition with each other, thereby applying during each cycle of operation an abrupt propulsion force to the confined liquid slug which becomes expelled as a very high-velocity liquid jet through ports in the housing. A calibrated control element for providing the proper pressures to the pneumatically-operated valve ensures proper movement of the shuttles.

8 Claims, 3 Drawing Sheets

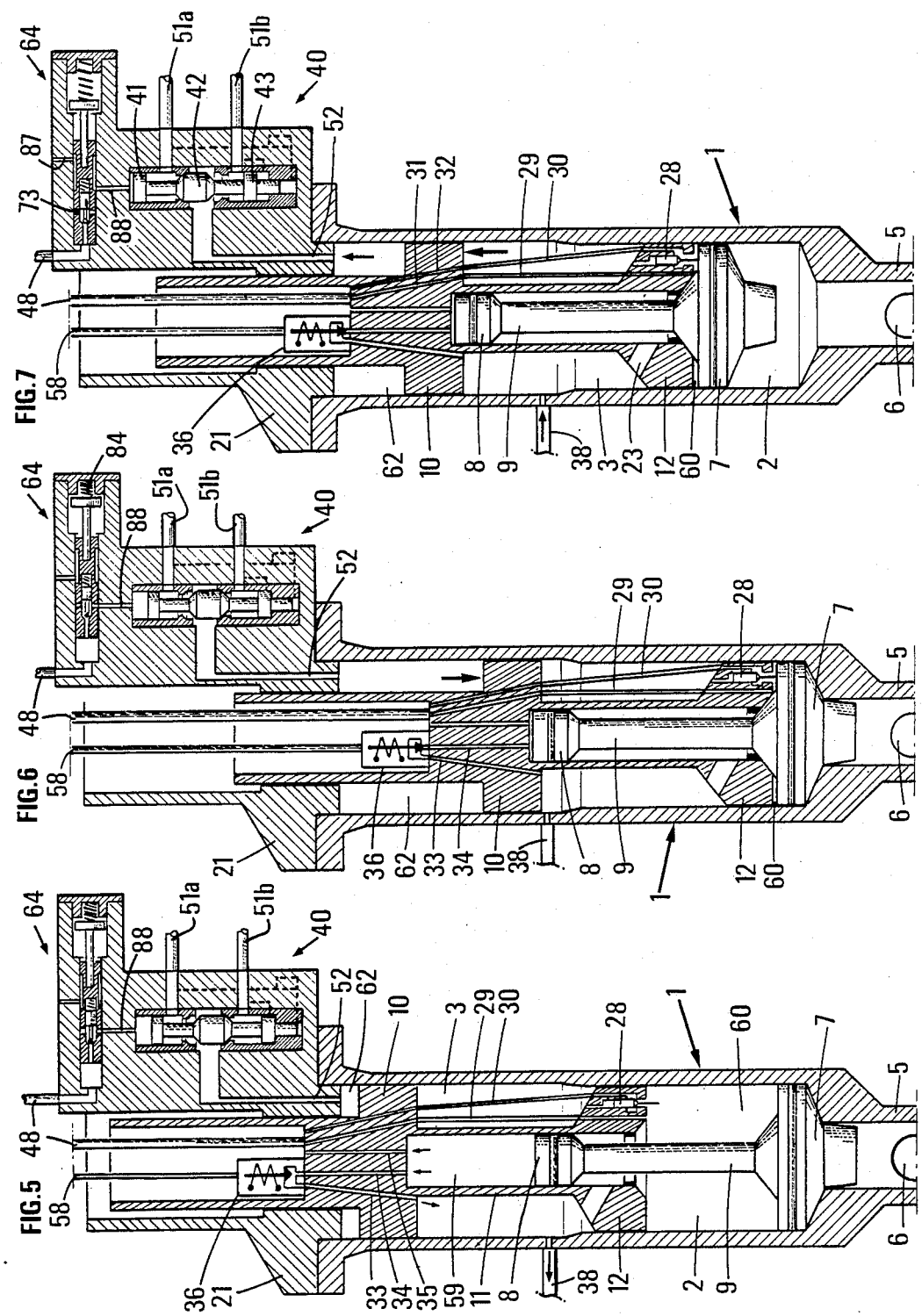

DEVICE FOR PRODUCING SOUNDWAVES IN WATER

This application is a continuation-in-part of my U.S. application Ser. No. 694,056 filed Jan. 23, 1985, now abandoned.

This invention concerns a improved apparatus of the water gun type for producing acoustical waves in water.

We know of an apparatus that generates acoustical waves in water, which includes a tubular body that opens in the outer middle at one of its ends, inside which a main piston can slide. The latter is connected to an auxiliary piston which forms an initial mobile unit. A system makes it possible to maneuver the initial mobile unit. It is comprised of a second mobile unit which includes a secondary piston and a ring-like piston which are suited for sliding inside the body and joined by a hollow rod inside which the auxiliary piston can slide, the mobile element being equipped with a central opening that acts as a seat for the main piston, and of means for producing fluids at an initial pressure and a second pressure that is higher than the first, those means working with a valve lifted by the application of the main piston against said seat. Pressure varies in the intermediate space between the main piston and the ring-like piston. Lifting of the valve places this space under low pressure. When it is shut, the same space is placed under said initial pressure.

The apparatus also includes a distribution sluice equipped with a mobile part (slide-valve) and channels for applying on one side of the secondary piston a fluid under the second pressure or low pressure, whether the mobile part is in a first or second position. The mobile part can be moved inside the sluice by the action of two antagonistic pressures, one of them being constant and applied to an initial side of the mobile part, the other being equal to the variable pressure that prevails inside the intermediate space between the main piston and the ring-like piston, and applied to a second side of the mobile part.

The means for producing the fluids include for instance a compressed air generator. The compressed air generator communicates constantly with the part of the body that is located between the secondary piston and the ring-like piston and with the inside of the hollow rod which connects them, regardless of the position of the latter. Such an apparatus is described for instance in the French patent application published as No. 2,558,600.

The application of high pressure results in the ungluing from one another of the ring-like piston and the main piston. Its entire surface is exposed to very high pressure. The first mobile unit is therefore boosted forward and it violently ejects outwardly the water that the body contains which triggers an implosion that produces seismic waves.

The intervention of the valve which makes it possible to alter, at the time of contact between the two mobile units, the pressures acting on the mobile part of the distribution sluice and thus to change the pressures applied to the secondary piston, and the selection of sections from the various elements that are subjected to pressures, results in rendering the rearming cycle totally automatic, the rearming phase being engaged as of the triggering of the apparatus.

The reverse movement of the main position to its rearming position can only be triggered if the ring-like piston has raised the valve, by leaning against it, and thus allowed the shift of the slide of the valve.

We noted when using this apparatus, especially as a result of ageing of gaskets around the pistons, that the second unit slides less easily inside the body and that its closing-in motion towards the main piston is no longer as obvious. The braking that can occur in the final phase of the closing-in can suffice so that the valve is partly raised while the main piston and the ring-like piston are not yet well applied one against the other. The drop in pressure between the two pistons which follows the partial raising of the valve can suffice for the distribution sluice to be activated. The two mobile units go backwards together towards the bottom of the body without being in contact one with the other. The moment of rearming of the apparatus is delayed. The disadvantages of a rearming delay are especially pronounced when we execute a multi-source seismic transmission system where several similar transmission apparatuses are towed under immersion and triggered according to a specific "firing" sequence.

The bad rearming of one of the two can have an impact in this instance on the global response to the transmission system.

We also found that the fault in the application of the second mobile unit against the main piston can even make the apparatus inoperative. That is because the pressure that prevails in the intermediate space can fluctuate sufficiently so as to entail a new shift in the initial mobile unit. The release in pressure that is produced in the chamber between the auxiliary piston (associated to the main piston) and the secondary piston (part of the second mobile unit) allows water inside. If the alternative pumping movement reoccurs, there can be enough water in that chamber to prevent the two mobile units from joining one to the other and the apparatus stops functioning, as we will see in greater detail at the end of the description that follows.

The apparatus according to the invention makes it possible to avoid the disadvantages that have been mentioned above.

It includes a tubular body that is open at the middle outside of one of its ends, a main piston, which slides inside the body, an auxiliary piston which is connected to the main piston and forms with it an initial mobile unit, a maneuvering system for the initial mobile unit comprised of a second mobile unit that includes a secondary piston and a ring-like suited for sliding inside the body and joined by a hollow rod inside which the auxiliary piston can slide, the ring-like being equipped with a central opening which acts as a seat for the main piston and means for producing fluids at an initial pressure and at a higher pressure than the first, those means cooperating with a thrust detector which is activated by the application of the main piston onto the ring-like piston. It also includes a slide-fitted distribution sluice of which the mobile part can be moved inside a cavity under the antagonistic effects of a fluid which is applied constantly under the second pressure and of a variable pressure, which can take on two different values depending on the placement of the thrust detector, that distributor being suited for applying intermittently a fluid under the second pressure to one side of the secondary piston.

It is characterized in that it includes a calibrated control element for applying to the mobile part of the distribution sluice, either said variable pressure which prevails in the intermediate space between the main piston and the ring-like piston when it is greater than threshold pressure, or a low pressure, which triggers the shift of the mobile part of said sluice.

The control element includes for instance a cylindrical cavity which communicates through a first and second duct respectively with the outside environment of the apparatus and with the inside of the distribution sluice towards the second side of its mobile element, an exposed rod towards a first end under calibrated force and towards the opposing end, under variable pressure prevailing in the intermediate space, the rod being equipped with recesses and being movable inside the cylindrical cavity from a position where the second duct communicates with the intermediate space and a position where it communicates with the first duct.

We verify during use that the control element which is inserted at the entrance of the distribution sluice makes it possible to prevent any movement of the two mobile units towards the rearming position so long as the pressure in the intermediate space has not dropped to a low value where we are sure that they are well applied to one another, and therefore to prevent unpredictable separation movements, which, as we have seen, can block the operation of the apparatus.

Other characteristics and advantages will surface in the course of the description of a preferred execution mode of the apparatus, and by referring to attached drawings wherein:

FIG. 5 is a schematic sectional view of the apparatus at the end of the triggering phase when the initial mobile unit has arrived at the end of its one-way course and the second mobile unit is in the process of joining it;

FIG. 6 is a schematic sectional view of the apparatus at a later moment when the second mobile unit has joined the first at the end of the run; and FIG. 7 is a schematic sectional view of the apparatus during the return phase of the two mobile units towards the rearming position.

Figures 1, 2:
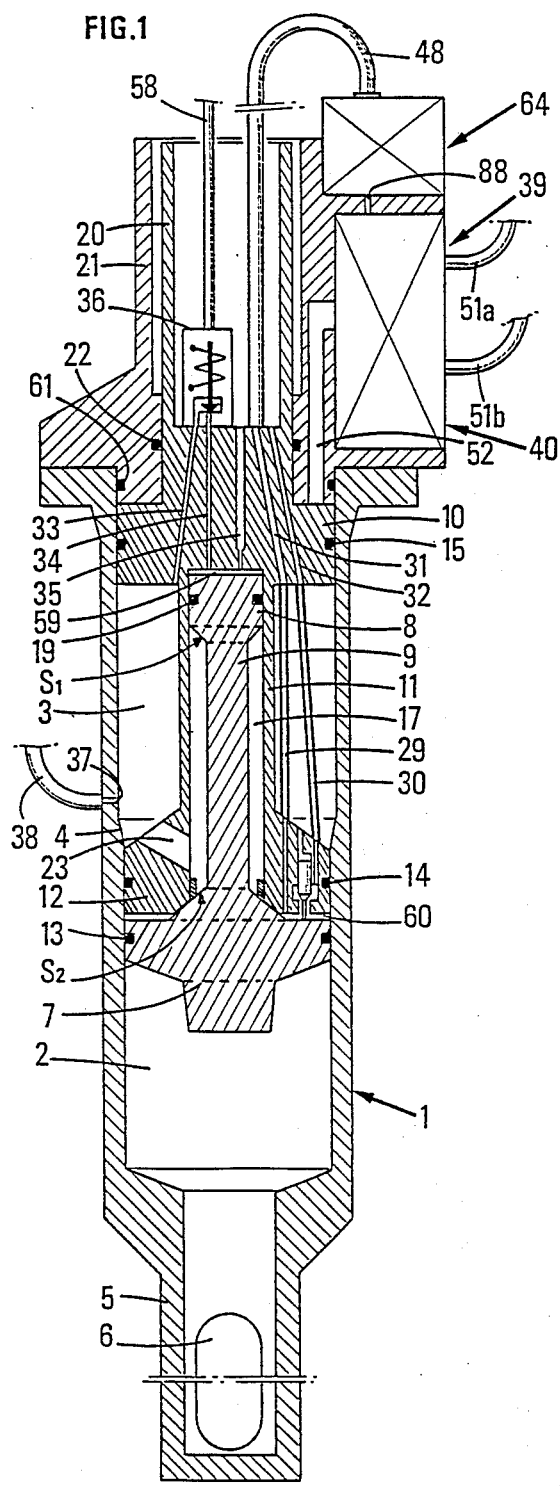
FIG. 1 is a schematic sectional depiction of the apparatus in its arming position which is also the rest position.
FIG. 2 is a more detailed sectional view of part of the ring-like piston which contains the thrust detector.

The device includes (FIGS. 1 to 4 especially) an extended tubular body 1 equipped with two coaxial chambers 2, 3 of varying sections that join to one another with a collar 4. Chamber 2 with the smaller section is open on the side opposing the collar 4 and communicates, through a tightened end part 5 of the body equipped with openings 6, with the outside medium. It also includes an initial mobile unit which is comprised of a main piston 7 and an auxiliary piston 9 fastened to the two ends of a first rod 9, and a second mobile unit comprised of a secondary piston 10 connected by a second rod 11 to a ring-like piston 12. The section of the main piston 7 and that of the ring-like piston 12 are equal to the section of the chamber 2. Ring-like joints 13, 14 are arranged on their periphery so as to make their sliding airtight. The section of the secondary piston 10 is suited to the section of chamber 3 of the body. A ring-like joint 15 is arranged on its periphery to make its sliding airtight inside chamber 3. The main piston 7 is connected to the rod 9 by a truncated part 16. A section bore 17 suited to the section of the auxiliary piston 9, is fitted in the truncated part 16 of the main piston 7. A joint 18a is fastened to the ring-like piston 12 in the vicinity of the chamferred part, in order to insulate well from the inside of the rod 11, the space 60 of the body included between the main piston 7 and the ring-like piston 12 when they are leaning on one another. The surface 52 of the main piston which is subjected to the action of compressed air, when it is in contact with the ring-like piston 12 and the joint 18a, is lower than the surface S1 facing the auxiliary piston 8. A ring-like joint 19 is arranged on the periphery of the auxiliary piston 8 in order to ensure the airtight sliding of the latter. The length of the rod 9 is such that, when the truncated part leans on the bevel 18, the auxiliary piston is more or less at the bottom of the central bore 17.

The secondary piston 10 includes a tubular extension 20, on the side opposite the ring-like piston 12. The body 1 is closed at its end opposing the tightened part 5, by a lid 21. A ring-like gasket 61 is arranged on the periphery of the lid. This lid is equipped with a central section bore suited to that of the tubular extension 20, at least on part of its length, this central bore including a peripheral groove for a gasket 22.

Figure 3:
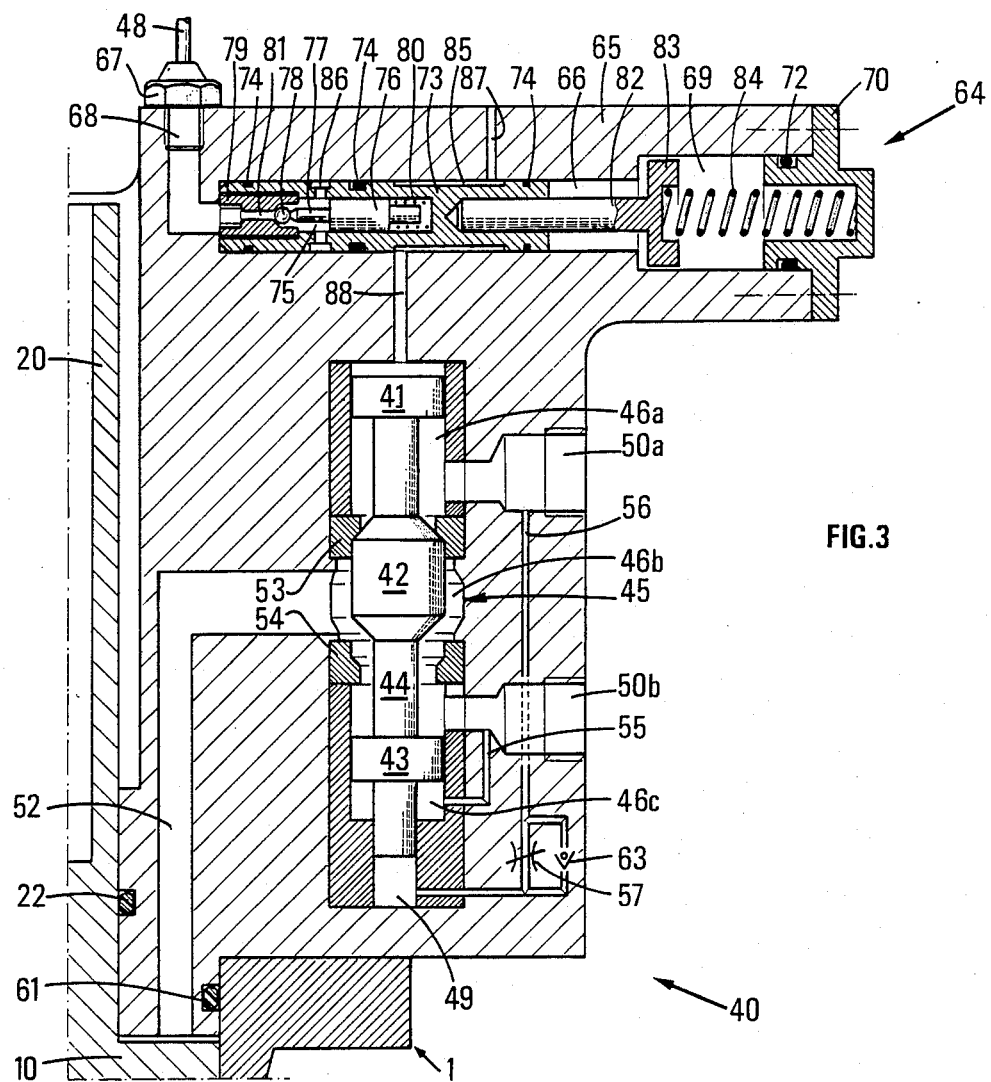
FIG. 3 is a schematic depiction of the slide-fitted distribution sluice and the control element fastened above it, for the intermittent application onto the secondary piston of a hydraulic fluid, the control element being in a rest position where pressure in the intermediate space has fallen below the threshold-value.
Figure 4:
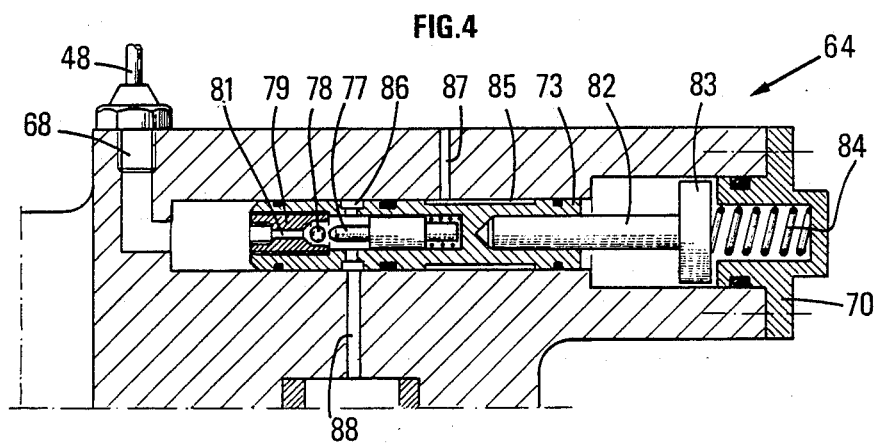
FIG. 4 is a partial view of the control element, which shows the position of the inner rod when the pressure in the intermediate space is higher than the threshold-value.

An opening 23 is performed inside the ring-like piston 12 to make the second chamber 3 communicate constantly with the central bore 17 of the second rod 11. Two ducts 24, 25 are provided in the ring-like piston 12 starting from the side 12a of the latter facing the secondary piston 10 (FIG. 3). The duct 24 crosses it from one end to the other. The other, 25, communicates with an inner recess 26 that leads inside the volume 60, on the opposite side 12b of the ring-like piston, through an orifice 27. Inside the recess 26 a control means can slide which is comprised of a needle valve 28 set up in order to insulate the duct 25 from the orifice 27, in rest position. The needle crosses the orifice 28 and protrudes outside the side 12b so that, when the ring-like piston 12 leans against the main piston, the needle is pushed and the valve 28 is raised, which sets up communication between the duct 25 and the intermediate space 60 between the two pistons 7 and 12.

The two ducts 24 and 25 communicate, by way of two pipes 29, 30, respectively with two ducts 31, 32 (FIG. 1) crossing from one end to the other the secondary piston 10 and leading inside the tubular extension 20 of the latter. Three other ducts 33, 34, 35 also cross the secondary piston from end to end. On one side, they lead inside the tubular extension 20 and two of them 33, 34 are connected with the two tracks of a two-track electrovalve 36. On the opposite side, one of the ducts 33 leads inside the ring-like space between the second hollow rod 11 and the outer wall of the body, and the two others 34, 35 lead inside that second rod inside a chamber 59 which is defined by the secondary piston 10 and the auxiliary piston 8. The duct 35 is very thin, at least on part of its length.

An opening 37 is performed inside the lateral wall of the body 1 at the level of the second chamber 3. A pipe 38 which is branched to a compressed air generator (not depicted), is connected to that opening 37, so as to sustain constantly high pressure (of about 140 bars for instance) in the part of the chamber 3 between the secondary piston and the ring-like piston 12.

The ring-like lid 21 at the end of the body 1 includes a part 39 (of which the detail is depicted in FIG. 3) in which a control system is placed which is basically comprised of a slide-fitted distribution sluice (or distributor) and a control element. This distributor 40 includes (FIG. 3) a slide comprised of three coaxial pistons 41, 42, 43 joined by the same rod 44 and movable inside a cavity 45 with three communicating chambers 46a, 46b, 46c. A bore 47 is provided through the wall of the lid 21. It has one of the lateral chambers 46a, communicating, by way of the control element (shown in FIG. 4, and described below) with a pipe 48 fastened at the orifice of the duct 31, at the bottom of the tubular recess 20. The lateral chamber 46c at the opposing end of the cavity 45, is extended by a tubular recess 49 which acts to guide the rod 44, at one of its ends. Two bores 51a, 51b (FIG. 1) lead inside the two opposing chambers 46a, 46c of the cavity to which two pipes are connected 51a, 51b (FIG. 1) that are linked to a known type of hydraulic system which is not shown, thus being suited to feed them oil respectively at high and low pressure (240 bars and 1 bar for instance).

A communication track 52 is set up between the intermediate or median chamber 46c and the end of chamber 3 of the body, on the side of the secondary piston 10 opposing the ring-like piston 12 (chamber 62, see FIG. 5).

The intermediate piston 42 of the slide includes two opposing truncated end parts. Two thrusts 53, 54 are arranged at the two ends of the median chamber 46b. Their shape is adapted to that of the truncated end parts of the piston 42, so that when the latter is applied successively against the thrust 53 (first position of the slide) and against the thrust 54 (second position of the slide) the median chamber 46b is well insulated from chamber 46a or chamber 46c. The piston 41 slides inside the chamber 46a by insulating one from the other the bores 47 and 50a, regardless of the position of the slide. The piston 43 slides inside chamber 46c. A duct 55 has the bore 50b communicating with the chamber 46c between the piston 43 and the bore 49 that extends the latter. The thickness of the piston 43 and the site where the duct 55 leads are selected so that, in the second position of the slide where the intermediate piston 42 is applied against the thrust 54, the piston 43 obstructs the entrance to the duct 55. Another duct 56 has the bore 50a communicating with the tubular recess 49, regardless of the position of the slide inside its cavity. A known type of calibrating means 57 is arranged inside the duct 56 to brake the oil flow. A reverse lock valve 63 is arranged in derivation on the calibrating means 57. The electrovalve 36 is controlled from a surface facility with a core cable 58.

A control element 64, according to the invention includes (FIG. 3) a cylindrical part 65 which is attached to the body of the distribution sluice 40 or mounted on it. This cylindrical part is equipped with a central cavity 66 closed at an initial end by a threaded cork 67. On a central bore 68 which crosses the cork 67 from end to end, we fasten an end of the channel 48 which is linked to its opposing end with the intermediate space 60 (FIG. 1). At its end opposite the threaded cork 67, the cavity 66 is extended by a second cavity with a larger section 69 that is closed by a mounted lid 70. A gasket 72 placed in a groove of the lid 70, insulates the two cavities 66, 69 from the medium outside of the apparatus. A rod 73 which is equipped at its periphery with gaskets 74, slides in airtight fashion inside the central cavity 66. The rod 73 includes on part of its length a bore 75 which is open on the side of the cork 67, where a piston can slide 76. A point 77 comes into contact with a bearing 78 that is placed inside a retainer at the end of a mounted connector 79. The piston 76 is pushed against that bearing by a spring 80. A duct 81 has the bottom of that retainer communicating with the central bore 68.

At the rod 73, on the side opposing the connector, a threaded rod 82 is fastened which is equipped with a head 83. A spring 84 is placed in the second cavity 69 between the head 83 and the lid 70. By screwing or unscrewing more or less the threaded rod 82, we tighten more or less the spring 84 and thus we make the force vary which is needed to push the rod 73 inside the central cavity.

On part of its length, the rod 73 includes a ring-like recess 85. A radial piercing 86 is provided inside the rod 73 and leads in the bore 75 at level with the point 77. In the wall of the control element 64 two ducts are pierced 87, 88. The first one 87, which is very thin has the central cavity 66 communicating with the outside medium. The second one 88 has the same central cavity communicating with the intake orifice 47 of the distribution sluice 40 through which the variable pressure is applied that can shift its slide.

The position of the ring-like recess 85 and its length are selected so that the ducts 87, 88 communicate with one another when the spring 84 is in rest position (FIG. 3). The position of the radial piercing is selected so that it communicates with the duct 88 in compression position of the spring 84.

The apparatus operates as follows:

The rest position of the apparatus, which corresponds to its arming position is that which is shown in FIG. 1. The second mobile unit is in its reverse position for which the secondary piston 10 is more or less in contact with the lid 21 of the body. The initial mobile unit is also in reverse position. In that position, the main piston 7 is leaning against the ring-like piston 12 and the needle valve 28 is raised. The ducts 24 and 25 communicate with the intermediate space 60, and subsequently, pressure equal to hydrostatic pressure, is exerted, by way of the pipe 48, on the rod 72 of the control element 64. The spring 84 sustains the control element in rest position (FIG. 3) and the chamber 46a of the distributor is under equi-pressure, through the ducts 74, 88 and the ring-like recess 85, with the outside medium. The slide is in the position shown in FIG. 3 to the extent that it is the low hydraulic pressure of the pipe 51b which is exerted by the channel 52 on the secondary piston 10 Since it is pushed from the opposing side by compressed air, it is sustained in reverse position. The main piston 7, because the needle valve is raised, is subjected to hydrostatic pressure on its two sides, except on its truncated part facing the central bore 17 where it is subjected to compressed air. The auxiliary piston 8 is subjected to hydrostatic pressure by way of the duct 35 and compressed air on its opposing side. The global force which is exerted on the initial mobile unit and that is the resultant of the forces applied by compressed air on the uneven surfaces S1 and S2, acts to maintain the main piston 7 applied against the joint 18a.

Then we order the opening of the triggering electrovalve 36 with an electrical impulse which puts the ducts 33 and 34 in communication with one another. Compressed air hence is admitted inside chamber 59 and is applied to the side of the auxiliary piston which faces the lid 21.

The new resultant of the forces exerted on the initial mobile unit leads to the separation of the second. The main piston 7 is leaves its seat 18 and the compressed air can be applied to its entire side facing the ring-like piston 12. The initial mobile unit is then suddenly boosted towards the end part 5 of the body against which it comes as a thrust (FIG. 5) and drives out of the openings 6 the water volume contained in the first chamber 2. The ejection of water at high speed produces in the outer medium powerful acoustical waves.

As soon as the initial mobile unit steers away from the second one, the needle valve 28 closes.

The pressure from compressed air inside the intermediate space 60 between the main piston 7 and the ring-like piston 12 (FIG. 1) is of about 140 bars for instance. This pressure which is applied by the channel 48, pushes back the rod 73 up to the position shown in FIG. 4 where the radial piercing 86 communicates with the duct 88. The compressed air penetrates inside the distribution sluice.

The ratio of the respective surfaces of the piston 41 and the rod 44 on the side of the recess 49, as well as the ratio of the compressed air and oil pressures being exerted in opposite direction from one another on the slide, are such that the latter moves towards its second position (FIG. 5) where the intermediate piston 42 leans against the seat 54, thus placing the duct 52 in communication with the bore 50a where high oil pressure prevails.

Since this high pressure which is applied to the side of the secondary piston 10 facing the lid 21 (chamber 62) is greater than the pressure of compressed air applied on its opposing side, the second mobile unit is in turn boosted to the end 5 of the body where it joins the initial one (FIG. 6).

Throughout the entire shifting phase of the two mobile units towards the end 5, the chamber 59 is maintained under overpressure which prevents any outside water intake.

When the second mobile unit joins the first one, the needle valve 28 is raised and pressure from the intermediate space 60 drops at a much lower value.

So long as that depleted pressure is greater than a threshold value of 5 to 10 bars for instance, it is applied to the slide of the valve 40. If it decreases below that value, the spring 84 pushes back the rod 73 towards the threaded cork 67 until the ducts 87 and 88 are put in communication (FIG. 3). The pressure that is applied to the valve on the side of the chamber 46a, drops to the value of the outer hydrostatic pressure and the slide of valve 40 shifts in earnest. The calibration means 57 makes it possible to delay its shift.

Fall of pressure in the chamber 62 leads to the bringing back of the second mobile unit towards the reverse position (FIG. 7). The resultant force which is applied to the initial mobile unit when the main piston 7 is in contact with the ring-like piston 12, which tends, as we have seen earlier, to apply the main piston 10 against it, the initial mobile unit follows the second one in its reverse motion up to their rearming position shown in FIG. 1. The apparatus is then ready for a new triggering.

The control element, by making the shifts of the slide more earnest, avoids unpredictable triggering that can occur so long as the pistons 8 and 12 are not totally applied one against the other and that the intermediate space 60 still communicates more or less with chamber 3 where high compressed air pressure prevails. In that instance, indeed, pressure in said space can drop to an average low value, of about 10 to 20 bars and fluctuate sufficiently for the slide which is directly subjected to that pressure, to shift in one direction and then in the opposite direction. The simultaneous rise of the two mobile units can be followed therefore by a separation, the initial mobile unit returning spontaneously towards the bottom.

The chamber 59 usually does not hold water. When a triggering is controlled by the intermittent opening of the electrovalve 36, compressed air penetrates inside the chamber 59 and prevents any water intrusion through the thin duct 35. In the absence of compressed air (usually supplied through the opening of the electrovalve), the spontaneous separation of the two mobile units produces the suction of water inside.

If the pumping movement is significant enough and repeated, it can follow that water which penetrated inside the chamber 59 prevents the initial mobile unit from completely reversing and coming in contact with the second one. The pressure inside the intermediate space remains too high, to allow the shift of the slide of the valve. The apparatus can no longer be rearmed.

The use of the control element 64 which prevents the combined shifts of the two mobile units towards their rearming position as long as they are not totally in contact one against the other, normalizes the operation and avoids risks of breakdown linked to water intakes.

I claim:

1. A improved apparatus for producing acoustical waves in water through sudden ejection of a liquid mass outside of a tubular body (1) which is open on the outer medium at one of its ends, this liquid mass being boosted by the sliding of a main piston (7) which is connected to an auxiliary piston (8) to produce an initial mobile unit, the apparatus including a maneuvering system for the initial unit comprised of a second mobile unit that includes a secondary piston (10) and a ring-like piston (12) which are adapted to slide inside the body and joined by a hollow rod (11) in which the auxiliary piston can slide, the ring-like piston being equipped with a central opening (17) that produces a seat for the main piston and, means to produce fluids at initial pressure and at a second pressure which is greater than the initial one, those means cooperating with a thrust detector (28) which is activated by the application of the main piston against the ring-like piston, and a slide-fitted distribution sluice (40) of which a mobile part is movable inside a cavity (46) under the antagonistic effects of a fluid under the second pressure that is applied constantly and a variable pressure, which can take on two different values according to the placement of the thrust detector, that distribution sluice being adapted to apply intermittently on one side of the secondary piston, a fluid under the second pressure, characterized in that it includes a calibrated control element (64) for applying to the mobile part of the distribution sluice (40), either said variable pressure that prevails in the intermediate space (60) between the main piston (7) and the ring-like piston (12) when it is greater than a threshold value, or a low pressure, which triggers the shifting of the mobile part of said valve.

2. An apparatus according to claim 1, characterized in that the control element includes a cylindrical cavity (66, 69) which communicates through an initial and second duct (87, 88) respectively with the medium outside of the apparatus and the inside of the distributor sluice (40) around the second side of its mobile element, a rod (73) which is exposed on the side of an initial end to a calibrated force and on the opposing side to said variable pressure, the rod (73) being equipped with recesses (85, 86) and being movable inside the cylindrical cavity between a position where the second duct (88) communicates with said intermediate space (60) and a position where it communicates with the first duct (85).

3. An apparatus according to claim 2, characterized in that the mobile rod includes, on the side of its second end, a central bore (75) where a reverse lock valve (76-79) can slide.

4. An apparatus according to claim 3, characterized in that it includes a calibrated spring (84) placed in the cavity (69) on the side of the initial end of the rod (73).

5. An apparatus according to claim 1, characterized in that the means for producing the fluids include a generator of compressed air under an initial pressure and a source of hydraulic fluid under a second pressure, the generator of compressed air communicates constantly with the part (3) of the body located between the second piston and the ring-like piston (12) comprising the second mobile unit, regardless of the position of the latter and the variable pressure applied to the control element is that which prevails in a circuit (24, 29, 31, 48) placed according to the position of the detector, under the pressure of the medium outside of the apparatus or with that of the generator of compressed air.

6. An apparatus according to claim 5, characterized in that the cavity (44b) of the distribution sluice (40) includes three coaxial chambers, the intermediate chamber (46b) communicating with one or the other of the two lateral chambers (46a, 46c) according to the position of a central piston (42) that is movable in the intermediate chamber, and the two lateral chambers communicating respectively with the low pressure circuit and the high pressure circuit of the hydraulic fluid source, in that the opposing ends of the slide bear uneven sections, the end with the largest section being exposed to variable pressure by way of the control element (64) and the other being exposed to high hydraulic pressure, and the ratio of the sections of the two opposing ends being selected so that the slide can move, when the variable pressure is that of compressed air, towards a position where the intermediate chamber (46b) communicates with the high pressure circuit of the hydraulic fluid source.

7. An apparatus according to claim 5, characterized in that the space (60) of the body included between the central piston (7) and the mobile element (12) is connected to the control element (64) by way of ducts (24, 31) which cross the ring-like piston and the secondary piston and pipes (29, 48).

8. An apparatus according to claim 1, characterized in that the space (59) in the hollow rod (11) included between the auxiliary piston (8) and the secondary piston (10) communicates constantly with the medium outside of the body by way of a thin duct (35) and intermittently, with a valve (36), with the part (3) of the body where the initial fluid pressure prevails constantly.

* * * * *